United States Patent
Van Hoven et al.

(10) Patent No.: US 10,448,922 B2
(45) Date of Patent: Oct. 22, 2019

(54) ROTATIONAL CATHETER WITH EXTENDED CATHETER BODY DRIVE SHAFT SUPPORT

(71) Applicant: Volcano Corporation, San Diego, CA (US)

(72) Inventors: Dylan E. Van Hoven, Oceanside, CA (US); Douglas E. Meyer, Folsom, CA (US)

(73) Assignee: VOLCANO CORPORATION, San Diego, CA (US)

( * ) Notice: Subject to any disclaimer, the term of this patent is extended or adjusted under 35 U.S.C. 154(b) by 753 days.

(21) Appl. No.: 14/103,582

(22) Filed: Dec. 11, 2013

(65) Prior Publication Data

US 2014/0171803 A1 Jun. 19, 2014

Related U.S. Application Data

(60) Provisional application No. 61/736,666, filed on Dec. 13, 2012.

(51) Int. Cl.
*A61B 8/00* (2006.01)
*A61B 8/12* (2006.01)

(52) U.S. Cl.
CPC .............. *A61B 8/4461* (2013.01); *A61B 8/12* (2013.01); *A61B 8/445* (2013.01)

(58) Field of Classification Search
None
See application file for complete search history.

(56) References Cited

U.S. PATENT DOCUMENTS

| 4,381,690 | A | * | 5/1983 | Kimble | G10D 13/065 |
| | | | | | 248/171 |
| 4,886,507 | A | * | 12/1989 | Patton | A61M 39/0613 |
| | | | | | 604/284 |
| 4,951,677 | A | * | 8/1990 | Crowley | A61B 5/6848 |
| | | | | | 600/109 |
| 5,174,157 | A | * | 12/1992 | Obermeier | G01L 9/0075 |
| | | | | | 73/715 |
| 5,586,968 | A | * | 12/1996 | Grundl | A61B 1/00151 |
| | | | | | 600/114 |

(Continued)

FOREIGN PATENT DOCUMENTS

JP   2000175917 A   6/2000
JP   2010533049 A   10/2010

(Continued)

OTHER PUBLICATIONS

International Search Report and Written Opinion received in Patent Cooperation Treaty Application No. PCT/US2013/074358, dated Mar. 31, 2014, 10 pages.

(Continued)

*Primary Examiner* — James M Kish

(57) ABSTRACT

In a rotational intravascular catheter, a proximal section of the catheter sheath, within which an elongated flexible drive member portion of the catheter is movably disposed, is extended into a telescoping portion of the catheter. The proximal sheath section functions to support the section of the drive member positioned within the telescoping section whether the telescoping section is in an extended position, qa retracted position, or any position therebetween.

16 Claims, 2 Drawing Sheets

(56) References Cited

U.S. PATENT DOCUMENTS

| | | | |
|---|---|---|---|
| 5,807,237 A * | 9/1998 | Tindel | A61B 1/313 600/114 |
| 2004/0073203 A1 | 4/2004 | Yu et al. | |
| 2005/0038335 A1* | 2/2005 | Gross | A61B 1/00082 600/407 |
| 2007/0021767 A1* | 1/2007 | Breznock | A61B 17/00234 606/185 |
| 2008/0167602 A1 | 7/2008 | Nita et al. | |
| 2009/0156941 A1* | 6/2009 | Moore | A61B 8/4461 600/467 |
| 2009/0163818 A1 | 6/2009 | Zelenka et al. | |
| 2010/0049099 A1 | 2/2010 | Thapliyal et al. | |
| 2010/0234736 A1 | 9/2010 | Corl | |
| 2011/0021911 A1* | 1/2011 | Waters | A61B 8/0883 600/439 |
| 2011/0224650 A1* | 9/2011 | Itou | A61B 8/12 604/524 |
| 2015/0152270 A1* | 6/2015 | Aizenberg | A61L 29/085 210/500.27 |

FOREIGN PATENT DOCUMENTS

| | | |
|---|---|---|
| JP | 2006525835 | 11/2016 |
| WO | 2009009799 A1 | 1/2009 |
| WO | WO 2010/009473 | 1/2010 |

OTHER PUBLICATIONS

International Searching Authority/European Patent Office, "Communication—Supplementary European Search Report," European Application No. 1386202.6 dated Jul. 19, 2016, 6 pages.

\* cited by examiner

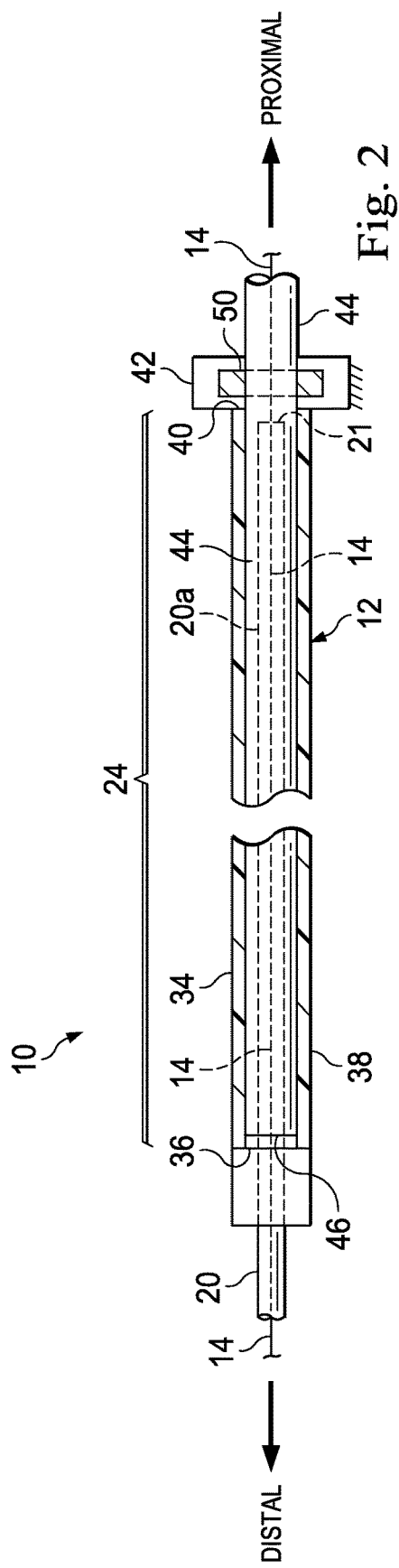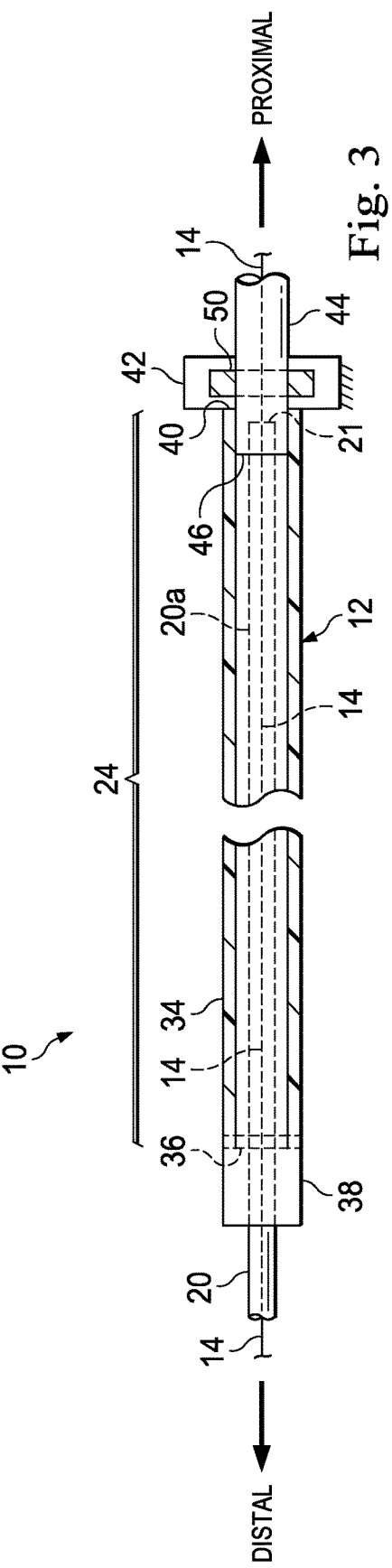

ROTATIONAL CATHETER WITH EXTENDED CATHETER BODY DRIVE SHAFT SUPPORT

CROSS-REFERENCE TO RELATED APPLICATION

The present application claims the benefit of the filing date of provisional U.S. patent application Ser. No. 61/736,666 filed Dec. 13, 2012. The entire disclosure of this provisional application is incorporated herein by this reference.

TECHNICAL FIELD

An embodiment of the present disclosure relates generally to the field of medical devices and, more particularly, to catheter apparatus used in internal vasculature diagnostic procedures.

BACKGROUND

Various techniques and systems have recently been developed to visualize the anatomy of vascular occlusions by using intravascular ultrasound (IVUS) imaging. IVUS techniques are catheter based and provide a real-time sectional image of the arterial lumen and the arterial wall. An IVUS catheter includes one or more ultrasound transducers at the distal tip of the catheter by which images containing cross-sectional information of the artery under investigation can be determined. IVUS imaging permits visualization of the configuration of the obstructing material and, in varying degrees, the boundaries of the intimal and medial layers of the arterial wall.

One common type of IVUS imaging catheter system typically includes an arrangement in which a single transducer at the distal end of the catheter is rotated at high speed (up to about 2000 rpm) to generate a rapid series of 360-degree ultrasound sweeps. Such speeds result in generation of up to about thirty images per second, effectively presenting a real-time image of the diseased artery.

The transducer is mounted on the end of a drive shaft or cable that is connected to a motor drive at the proximal end of the catheter. The rotating transducer is housed within a sheath that does not interfere with the ultrasound and protects the artery from the rapidly spinning drive shaft. Thus, an IVUS imaging (or "sensing") catheter may be advanced to the region of an occlusion using conventional angiographic techniques and then may be operated to provide real-time sectional images of the vascular lumen in the arterial wall, including the occluding material and intimal and medial layers of the artery wall. Other types of catheter-based systems for use in visualizing the internal anatomy of body portions implementing sheath-enclosed movable sensing/imaging elements disposed on elongated drift shaft structures are also known, including photo-acoustic, optical coherence tomography, phased array/multiple transducer, and spectroscopic systems.

Medical sensing catheters of these representative types comprise a tubing assembly through which the drive cable movably extends, the tubing assembly typically including a sheath insertable into the patient and having a proximal end fixed to a telescope section which permits the drive cable, and thus the sensor, to be selectively moved though the patient's body via the interior of the inserted sheath which remains stationary in the patient's body. The telescope section comprises a tubular outer catheter or telescope member, to the distal end thereof the proximal end of the sheath is anchored. The telescope section also has a tubular inner catheter or telescope member which telescopes into the interior of the outer telescope member through its proximal end and is movable through the interior of the outer telescope member between retracted and extended positions relative to the outer telescope member. The drive cable is secured to the inner telescope member for longitudinal movement therewith relative to the outer catheter member.

Distal movement of the inner telescope member toward its retracted position distally pushes the drive cable and the sensor through the sheath, and proximal movement of the inner telescope member toward its extended position pulls the drive cable and the sensor back through the sheath. When the inner telescope member is moved to its extended position a portion of the drive cable extending through the interior of the outer catheter member between the distal end of the outer telescope member and the distal end of the inner catheter member is substantially unsupported and unconstrained within the telescope section.

In response to a subsequent movement of the inner telescope member distally toward its retracted position the exposed, unsupported portion of the drive cable may undesirably be caused to buckle within the telescope section, thereby hindering a desired distal advancement of the drive cable through the sheath and potentially damage the cable. A previously proposed solution to this potential drive cable buckling problem has been to position a separate reinforcing structure within the telescope section to support the portion of the drive cable extending through the telescope section when the inner telescope member is moved away from its retracted position.

This previously proposed drive cable supporting technique, however, has proven to be less that wholly satisfactory because it requires the provision and installation in the overall catheter assembly of at least one additional component, thereby undesirably increasing the catheter assembly cost, complexity and manufacturing time. As may be readily seen from the foregoing, a need exists for an improved solution to the above-described catheter drive cable buckling problem. It is to this need that the present invention is primarily directed.

BRIEF DESCRIPTION OF THE DRAWINGS

FIG. 2 is a longitudinally foreshortened schematic cross-sectional view through a telescope section of the catheter apparatus with an inner telescope portion of the section being in its fully retracted position; and FIG. 3 is a view similar to that in FIG. 2 but with the inner telescope portion of the telescope section being in its fully extended position.

DETAILED DESCRIPTION

Figure 1:
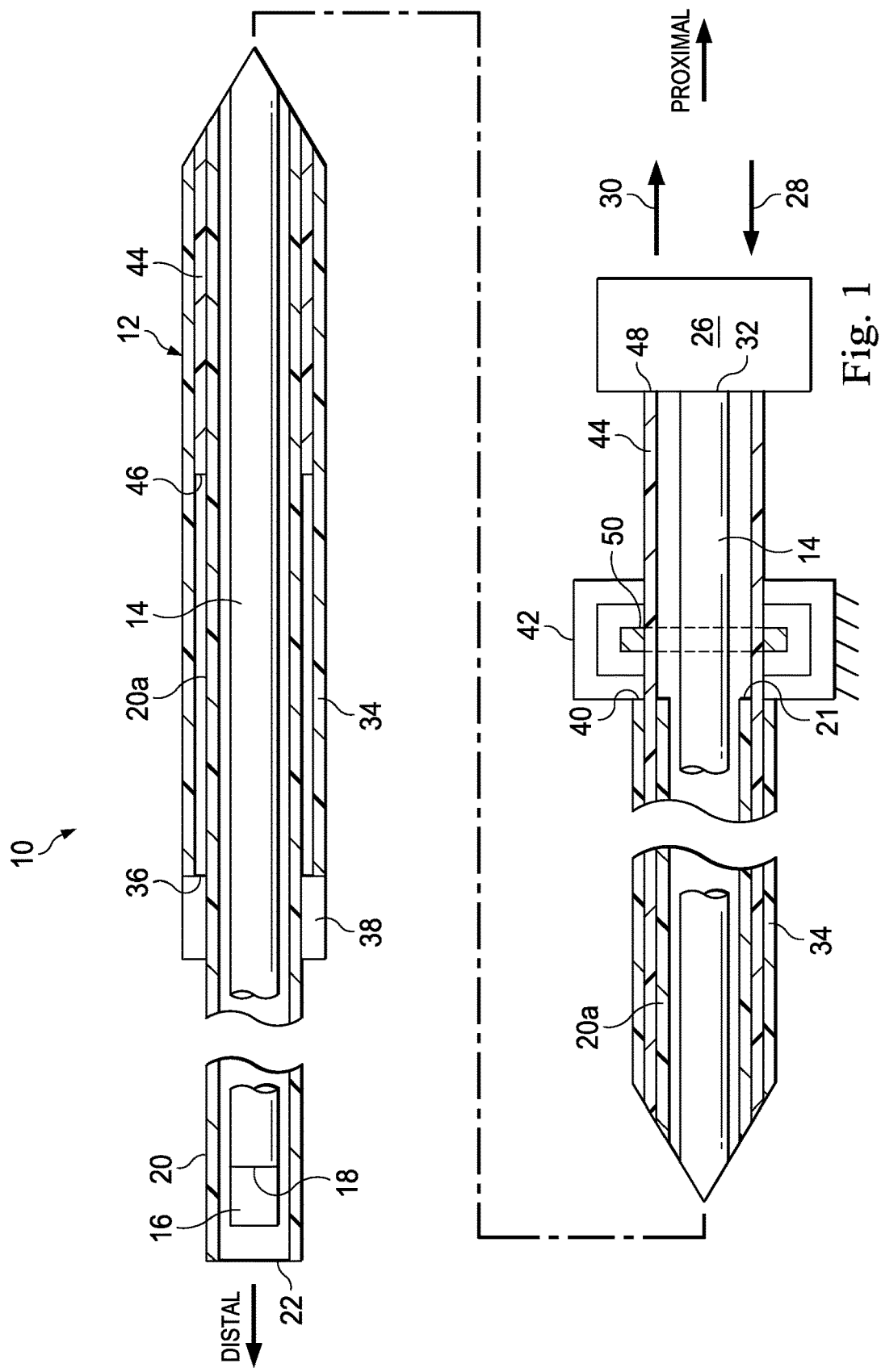
FIG. 1 is an enlarged scale longitudinally foreshortened schematic cross-sectional view through medical sensing catheter apparatus embodying principles of the present invention.

A catheter 10 embodying principles of the present invention is schematically depicted in FIGS. 1-3. By way of non-limiting example, the catheter apparatus 10 is a medical sensing catheter, and more specifically is an intravascular ultrasound (IVUS) imaging catheter. Catheter 10 includes an elongated flexible tubular assembly 12 that circumscribes an elongated flexible drive shaft or cable 14 having an ultrasound sensor 16 on its distal end 18. Drive cable 14 is illustratively of a conventional helically wound wire construction.

The tubular assembly 12 that circumscribes the drive cable 14 and the sensor 16 includes a sheath 20 having a proximal end 21, and a distal end 22 insertable into the body of a patient, and a telescope section 24 (see FIGS. 2 and 3) that facilitates movement of the drive cable 14 distally and proximally through the sheath 20 while it remains stationary within the patient's body. Selective rotation and translation of the drive cable 14 relative to the sheath 20 is effected by a conventional, schematically depicted translational/rotational drive mechanism 26 (FIG. 1) that may be selectively translated in distal and proximal directions as respectively illustrated by arrows 28,30 in FIG. 1. The drive mechanism 26 is operatively coupled to the proximal end 32 of the drive cable 14 and functions in a conventional manner to translate and rotate the drive cable 14.

Telescope section 24 includes an elongated flexible tubular outer catheter or telescope member 34 having a distal end 36 fixedly secured to an annular coupling 38 that circumscribes and is fixedly secured to a longitudinally intermediate portion of the sheath 20. The proximal end 40 of the outer telescope member 34 is anchored to a schematically depicted stationary support structure 42 distally positioned relative to the drive mechanism 26. The telescope section 24 further includes an elongated flexible tubular inner catheter or telescope member 44 which has distal and proximal ends 46,48. Proximal end 48 is secured to the drive mechanism 26, and the inner telescope member 44 slidably extends through an O-ring seal member 50 carried by the stationary support structure 42 which may be of a conventional construction and may be assembled around the O-ring 50.

According to a feature of the present invention the O-ring seal 50 is formed of a self-lubricating material, representatively a fluoroelastomeric material. The use of a self-lubricating seal member substantially facilitates and quickens the assembly of the support structure 42 by eliminating the necessity of lubricating the seal and one or more of the support structure parts prior to using the support structure 42.

As shown in FIGS. 1-3, the inner telescope member 44 is distally telescoped into the outer telescope member portion 34 of the overall tubular assembly 12 for translation relative thereto (by means of the drive mechanism 26) between a retracted position shown in FIG. 2 (in which the sensor 16 is distally advanced within the sheath 20) and an extended position shown in FIG. 3 (in which the sensor is proximally retracted within the sheath 20).

According to a further feature of the present invention, a proximal end portion 20a of the sheath 20 extends through the coupling 38 into the interior of the outer telescope member 34 and proximally telescopes into the distal end of the inner telescope member 44 within the telescope section 24. Thus the proximal sheath section 20a directly supports the portion of the flexible drive cable 14 within the telescope section 24 whether the inner telescope member 44 is in its retracted position, its extended position, or any position therebetween.

This support for the portion of the flexible drive cable 14 within the telescope section 24, that prevents potential buckling of such cable portion when the drive cable 14 is being distally pushed by the inner telescope member 44 as it is moved toward its retracted position, is desirably achieved without the previous additional manufacturing and assembly cost of providing and installing a separate support structure within the telescope section 24. In the present invention this cable support function is uniquely provided using a longitudinal portion of the sheath 20 which may be simply furnished in a bit longer length to form the cable support portion 20a thereof. Illustratively, the sheath 20 is of a continuous one piece construction, and need not be modified in any manner other than the illustrated lengthening.

While the catheter 10 has been representatively illustrated as being an IVUS catheter, it will be readily appreciated by those of ordinary skill in this particular art that other types of catheter structures with flexible internal drive shafts or cables and associated telescope sections may advantageously incorporate the above-described type of cable support without departing from principles of the present invention. Such other types of catheter structures include, for example, photo-acoustic, optical coherence tomography, phased array/multiple transducer, and spectroscopic systems.

What is claimed is:

1. Medical sensing catheter apparatus comprising:
   an elongated flexible sheath comprising a distal end and a proximal end;
   an elongated flexible drive structure longitudinally extending through an interior of said sheath and being movable relative thereto, said drive structure comprising a distal end portion with a sensor disposed thereon, wherein the sensor is operative to generate signals useable to create diagnostic information with respect to a patient body area;
   an elongated flexible tubular inner catheter member arranged externally to said sheath, said inner catheter member being distally and proximally movable along said sheath between fully extended and fully retracted positions thereon;
   an elongated flexible tubular outer catheter member arranged externally onto said elongated flexible tubular inner catheter member, said outer catheter member comprising a proximal end secured to a stationary support structure, and a distal end secured to an annular coupling, wherein the annular coupling is secured to said sheath at a location intermediate said distal and proximal ends of said sheath, wherein the elongated flexible tubular inner catheter member is distally telescoped externally onto a proximal end portion of said sheath extending proximally through said outer catheter member; and
   wherein an inner catheter member diameter is less than an outer catheter member diameter and the inner catheter member slidably extends through an O-ring member, said O-ring member located in an interior of the stationary support structure,
   wherein an outer diameter and a length of the annular coupling is smaller than an outer diameter and a length of the stationary support structure, and
   wherein the distal end of the elongated flexible sheath is positioned distally of the annular coupling and is configured to be inserted into the patient body area.

2. The medical sensing catheter apparatus of claim 1 wherein said sensing element is a rotatable ultrasonic sensing element.

3. The medical sensing catheter apparatus of claim 2 wherein said elongated flexible drive structure is of a wound wire construction.

4. The medical sensing catheter apparatus of claim 1 wherein said sheath is of a joint-free configuration from its distal end to its proximal end.

5. The medical sensing catheter apparatus of claim 1 wherein the O-ring member is self-lubricating.

6. The medical sensing catheter apparatus of claim 1 wherein said O-ring member is of a fluoroelastomeric material and is disposed proximally of said proximal end of said outer catheter member.

7. The medical sensing catheter apparatus of claim 1 wherein said sheath and said flexible drive structure are structurally arranged to facilitate operational rotation of said flexible drive structure relative to said sheath at speeds up to 2000 rpm.

8. Catheter apparatus comprising:
an elongated flexible tubing assembly comprising:
a telescope section including a tubular outer telescope member comprising proximal and distal ends, wherein the proximal end is secured to a stationary support structure and the distal end is secured to an annular coupling, the stationary support structure comprising an O-ring member on an interior of the stationary support structure;
a tubular inner telescope member longitudinally movable through an interior of said outer telescope member toward and away from said distal end thereof, wherein the tubular inner telescope member slidably passes through the O-ring member;
a sheath member anchored to said outer telescope member and comprising a distal end portion and a proximal end portion, the proximal end portion extending proximally through said outer telescope member and telescopingly received within an interior of said inner telescope member, wherein an inner telescope member diameter is less than an outer telescope member diameter; and
an elongated flexible drive member movable relative to said flexible tubing assembly and extending through said catheter, said outer telescope member and said inner telescope member and being supported within said outer telescope member by said proximal end portion of said sheath member,
wherein an outer diameter and a length of the annular coupling is smaller than an outer diameter and a length of the stationary support structure, and
wherein the distal end portion of the sheath member is positioned distally of the annular coupling and is sized and shaped for positioning within a vessel of a patient.

9. The catheter apparatus of claim 8 further comprising an ultrasound sensor carried on said distal end of said flexible drive member for rotation therewith relative to said flexible tubing assembly.

10. The catheter apparatus of claim 9 wherein said flexible drive member is of a helically wound wire construction.

11. The catheter apparatus of claim 8 wherein said sheath is of a joint-free configuration from its distal end to its proximal end.

12. The catheter apparatus of claim 8 wherein the O-ring member is self-lubricating.

13. The catheter apparatus of claim 12 wherein said O-ring member is of a fluoroelastomeric material.

14. Medical catheter apparatus comprising:
a tubular outer catheter member comprising proximal and distal ends, wherein the proximal end is secured to a stationary support structure and the distal end is secured to an annular coupling, wherein the stationary support structure includes an O-ring member in an interior of the stationary support structure;
a tubular inner catheter member comprising proximal and distal ends, said inner catheter member being telescoped into said outer catheter member, through said proximal end thereof, for axial movement through said outer catheter member between retracted and extended positions relative to said outer catheter member, wherein said inner catheter member slidably passes through said O-ring member;
a sheath longitudinally extending distally away from said distal end of said outer tubular catheter member and comprising a proximal portion extending through said outer catheter member, wherein the sheath is positioned within an interior of the tubular inner catheter member; and
an elongated flexible drive member extending through and being movable relative to said outer catheter member and said sheath, said proximal portion of said sheath supporting said flexible drive member within said outer catheter member, and being telescoped into said distal end of said inner catheter member,
wherein an inner catheter member diameter is less than an outer catheter member diameter,
wherein an outer diameter and a length of the annular coupling is smaller than an outer diameter and a length of the stationary support structure, and
wherein a distal end of the sheath is positioned distally of the annular coupling and is configured to inserted into a patient body area.

15. The medical catheter apparatus of claim 14, wherein the sheath longitudinally extends proximally into the inner catheter member without longitudinally extending proximally past the stationary support structure.

16. The medical catheter apparatus of claim 15, wherein a proximal end of the sheath is aligned with the stationary support structure.

* * * * *